United States Patent
Dos Santos et al.

(10) Patent No.: US 7,622,933 B2
(45) Date of Patent: Nov. 24, 2009

(54) ELECTRODE

(75) Inventors: Ulysse S. Dos Santos, Burnaby (CA); Manpreet S. Sidhu, North Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 190 days.

(21) Appl. No.: 11/903,644

(22) Filed: Sep. 24, 2007

(65) Prior Publication Data

US 2009/0078386 A1   Mar. 26, 2009

(51) Int. Cl.
*G01R 27/28* (2006.01)
*D21F 7/06* (2006.01)
*C02F 1/00* (2006.01)

(52) U.S. Cl. .................. 324/649; 162/263; 210/746
(58) Field of Classification Search ................ 324/649; 162/49, 263; 73/53.03, 61.43, 61.41; 210/746
See application file for complete search history.

(56) References Cited

FOREIGN PATENT DOCUMENTS

| JP | 55-154454 A | 12/1980 |
|----|-------------|---------|
| JP | 63-42458 A | 2/1988 |
| JP | 08-170956 A | 7/1996 |
| JP | 10-282034 A | 10/1998 |
| JP | 2001-208710 A | 8/2001 |
| KR | 1020040090431 A | 10/2004 |

OTHER PUBLICATIONS

JP 2001-208710 (machine translation of complete document) Note: IDS of May 18, 2009 only referenced the English language abstract.*
JP 08-170956 (machine translation of complete document) Note: IDS of May 18, 2009 only referenced the English language abstract.*

* cited by examiner

*Primary Examiner*—Matthew O Savage
*Assistant Examiner*—Paul J Durand
(74) *Attorney, Agent, or Firm*—Munck Carter, LLP (57) ABSTRACT

An apparatus and method for sensing characteristics of a liquid are disclosed. The exemplary embodiment may have an electrode for transmitting electrical signals associated with characteristics of the liquid to and from the liquid. The electrode may have an aperture on the interior of the electrode with the aperture surface in contact with the liquid. The electrode may have a sensor portion in contact with the liquid and a coupling portion with a tapered thread. The electrode may contain an electrical coupling on the isolated outer surface of the electrode for communicating the electrical signal from the electrode.

20 Claims, 7 Drawing Sheets

EXPLODED VIEW

ASSEMBLED VIEW

EXPLODED VIEW

ELECTRODE

FIELD OF THE INVENTION

The present invention relates generally to sensing characteristics of a liquid. More particularly, the present invention relates to an apparatus and method for utilizing an electrode to sense characteristics of a liquid.

BACKGROUND

Paper mills produce paper through a wood pulping process that begins with wood chips as the raw material. The wood chips are initially broken down or digested into wood fibers, which are then passed on for further processing to produce a variety of paper-based products. During the process of "digesting" the wood chips, a caustic solution referred to as white liquor is added to the wood chips. The white liquor is typically composed of mainly sodium sulfide ($Na_2S$) and sodium hydroxide (NaOH). At the end of the "digesting" process, chemical reactions, which have produced the desired wood fibers, have also produced a different caustic solution which is now referred to as black liquor. As a secondary process to minimize waste and optimize production, the black liquor may be recovered and chemically converted first to a green liquor and then back to a white liquor. The recycled white liquor may now be re-used in the digestion of another batch of wood chips.

The black liquor may be burned in a boiler, which leaves a smelt. This smelt is dissolved in water or "weak wash liquor" to produce green liquor. This conversion is often referred to as the "causticizing process" or the "causticizing reaction." The causticizing process takes place in a "slaker" where "causticizing agents," such as lime, are added during the conversion back to white liquor. The causticizing process can be optimized by proper control of the flow rate of the green liquor into the slaker and proper control of the quantity and frequency of the addition of the causticizing agent.

During the processing it is extremely beneficial to monitor the chemical composition of the changing liquor. One method of controlling the composition of the liquor during the causticizing process is to embed electrodes in the tank containing the liquor. This method is effective; however, the caustic solution that surrounds the electrodes can have adverse effects on the electrodes, such as fluctuations or inaccurate readings from the electrodes and physical deterioration of not only the electrode surfaces but also any seals around the electrodes. Both of these seals have short lifespans when exposed to the caustic pulp liquor. Any required maintenance and/or replacement of the electrodes may involve manual control of the liquor composition or a suspension of the paper mill processing. Accordingly, there exists a need to extend the usable life of the electrodes used to measure the characteristics of the highly caustic pulp liquor.

Some methods to isolate the electrodes from the liquor include the use of elastomeric or glass seals. Both of these seals may have short lifespans when exposed to the caustic pulp liquor. Any required maintenance and/or replacement of the electrodes may involve manual control of the liquor composition or a suspension of the paper mill processing. Accordingly, there exists a need to extend the usable life of the electrodes used to measure the characteristics of the highly caustic pulp liquor and provide for the replacement of the electrodes.

SUMMARY OF THE INVENTION

The present invention solves these and other needs by providing a method and apparatus for sensing characteristics of a liquid by using electrodes containing interior apertures. An exemplary embodiment may provide improved o-ring insulation to seal and isolate the electrodes from the liquid.

In an exemplary embodiment of the invention, an electrode is used for transmitting electrical signals associated with characteristics of a liquid to and from the liquid. The thin electrode has an aperture on the interior of the electrode, and the aperture surface is in contact with the liquid. An electrical coupling contained on an isolated outer surface of the electrode is used for communicating an electrical signal from the electrode.

In another embodiment where conditions require more than one electrode, the electrodes may be stacked alternately with o-rings. The electrodes and o-rings may be compressed together to seal the surfaces exposed to the liquid from the outer surfaces containing the electrical couplings. The apertures of the electrodes align to form a cavity where the liquid comes into contact with the electrodes. In another embodiment, a cleaning solvent supply orifice may direct cleaning solvent across the aperture surface of the electrodes and O-rings to remove any accumulations on this surface.

BRIEF DESCRIPTION OF THE DRAWINGS

The above and other objectives and advantages of the present invention will be apparent upon consideration of the following detailed description, taken in conjunction with the accompanying drawings, in which like reference numbers refer to like parts throughout, and in which.

DETAILED DESCRIPTION

Figure 1:
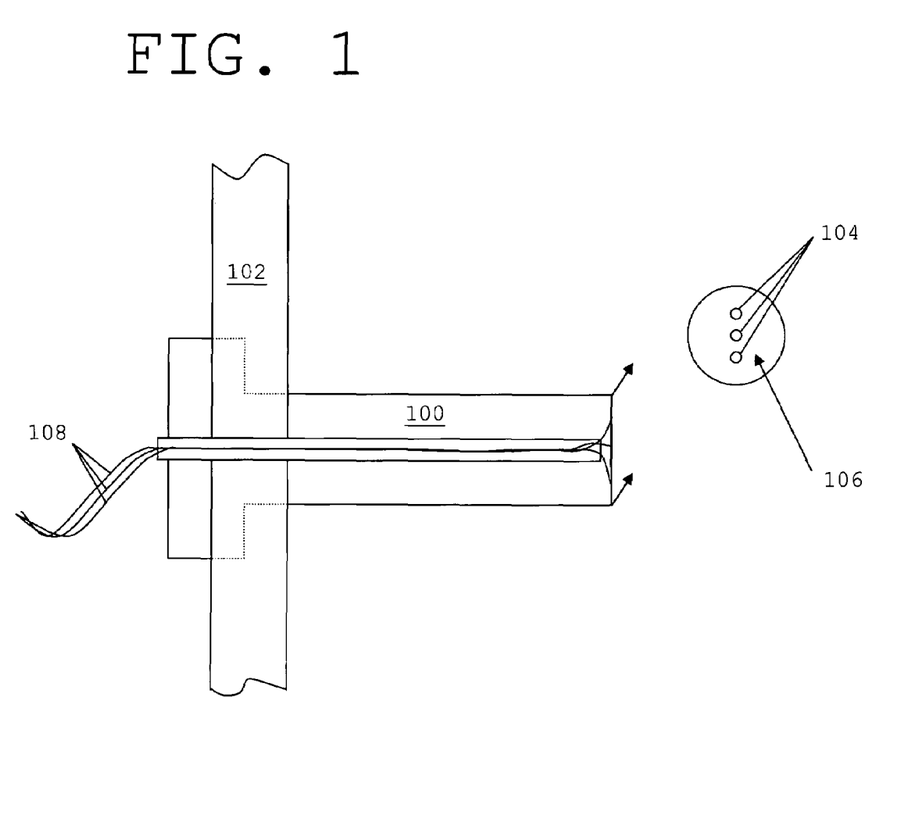
FIG. 1 is a generalized schematic of an electrode.

Referring to FIG. 1, an electrode arrangement and electrode housing are used to transmit electrical signals from a liquid within a container, for example, a pipe, tank, or shipping container. At one end, an electrode housing 100 is sealably mounted in a digester or recausticizing tank 102. The specific location of the electrode housing within the tank may be based on the preferred location of sampling and/or location of material within the tank.

The sensing end 106 of the electrode housing 100 extends into the tank 102. As shown in the cross-sectional view, electrodes or probes 104 may be mounted flush with a surface of the sensing end 106. The electrodes 104 are in direct contact with the liquid in the recausticizing tank 102. Wires 108 extend from the electrodes 104 through the electrode housing 100 and out of the tank 102 to transmit readings to receiving equipment outside of the tank. One possible electrode configuration is described in U.S. Pat. No. 6,235,123 issued May 22, 2001, entitled "Chemical Cleaning System for Electrodes Used in a Liquid Environment," which is incorporated herein by reference.

Figure 2:
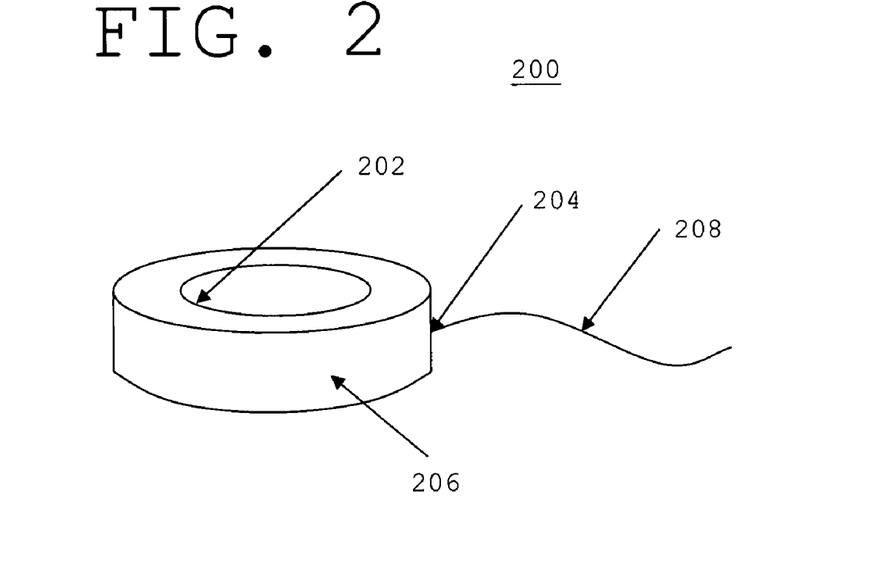
FIG. 2 is a generalized schematic of the electrode according to a first exemplary embodiment of the invention.

Referring to FIG. 2, an exemplary electrode 200 for sensing characteristics of a liquid is shown. The electrode 200 contains an interior aperture 202 through the center portion of the electrode 200. In this exemplary embodiment, the interior aperture 202 is circular in shape; however, the shape of this interior aperture 202 may be any regular or irregular shape. It is the surface of the interior aperture 202 that may be in contact with the liquid being analyzed. On an isolated exterior surface 206 of the electrode 200, an electrical coupling 204 communicates the electrical signal from the electrode 200 through a wire 208 routed to receiving equipment outside of the tank.

In an exemplary embodiment, the thickness of the electrode 200 may be about 4-8 mm although it is not limited to this range. The diameter of the electrode 200 may be about 25-50 mm although it is also not limited to this range. The electrode 200 has a circular outer shape; however, the outside shape of the electrode 200 is not limited to this shape. The electrode 200 may be composed of platinum or another inert conductive material, such as gold, graphite, iridium, palladium, or carbon. Other materials such as stainless steel and titanium are possible in certain situations.

Figure 3:
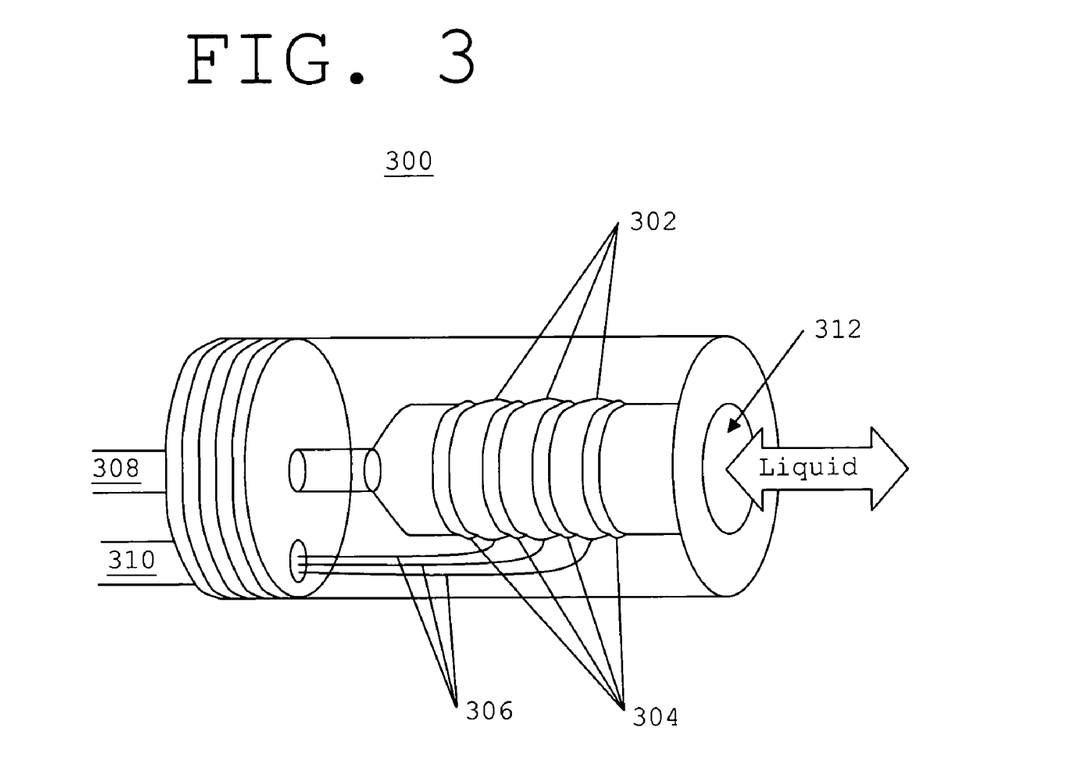
FIG. 3 is a generalized schematic of an electrode housing design, including a cleaning system, according to a second exemplary embodiment of the invention.

Referring to FIG. 3, an exemplary embodiment of an electrode housing 300 is shown. Electrodes 302 may be similar to the individual electrode 200 previously described. The electrodes 302 may be assembled to provide the electrode housing 300. Each electrode 302 is separated from an adjacent electrode 302 by an o-ring 304. In this exemplary assembly, there are three electrodes 302 and four o-rings 304. However, the electrode housing is not limited to any specific quantity or arrangement of electrodes 302 or o-rings 304. The electrodes 302 and the o-rings 304 are aligned and stacked together alternately. This allows the electrodes 302 to be isolated from one another.

The liquid to be analyzed flows through a cavity 312 in the electrode housing 300 and comes into contact with the interior aperture of an electrode 302 (such as with the surface of the interior aperture 202 shown in FIG. 2). The electrical signal generated and/or received by the liquid is transmitted from the interior aperture surface through the electrode 302 to wires 306. The electrode housing 300 allows the electrical signal to be transmitted from a harsh environment to the wires 306. The wires supply the electrical signal to receiving equipment. One possible example of receiving equipment is described in U.S. Pat. No. 6,416,651 issued Jul. 9, 2002, entitled "Multi-Electrode Composition Measuring Device And Method," which is incorporated herein by reference.

In the exemplary embodiment, the electrodes 302 and the o-rings 304 are compressed together to isolate the outer surfaces of the electrodes 302 where the electrical couplings are located. This may be accomplished in a variety of ways. For example, the electrodes 302 and the o-rings 304 may be compressed between a top and a bottom plate (not shown). The electrodes 302 and the o-rings 304 may be fitted within cylindrical rings within a cylindrical housing. The electrodes 302 may rely on a compression fit to hold the electrodes 302 in place during operation. In another example, the electrodes 302 may have a threaded exterior surface that may be screwed into a cylindrical housing with a threaded interior surface. Embodiments are not limited to the above constructions. A variety of constructions will be apparent to an individual skilled in the art.

The o-rings 304 may contain urethane to help minimize the damaging effects of the caustic pulp liquor used in paper processing. The design and material of the O-rings 304 may be selected based on the desired operation environment and/or insulating need of the electrodes 302.

Figure 4:
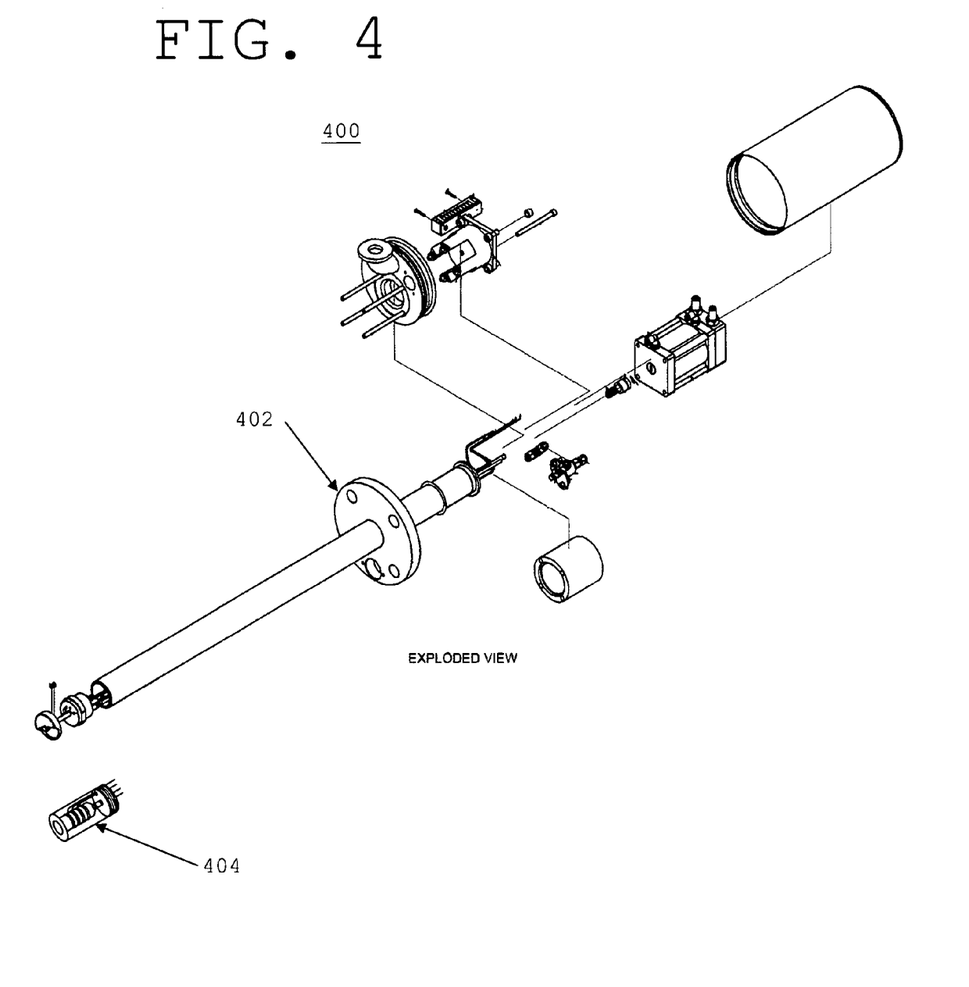
FIG. 4 is an exploded view of a sensor housing design, including a cleaning system, according to an exemplary embodiment of the invention.

According to one exemplary embodiment, the electrode housing 300 contains a cleaning solvent supply orifice 308. The cleaning solvent supply orifice 308 directs a cleaning solvent across the interior aperture of an electrode 302 (such as across the surface of the interior aperture 202 shown in FIG. 2) to remove any accumulations on this surface. The cleaning solvent applied in this manner minimizes the damaging effects on the electrodes 302 due to caustic pulp liquor used in the Pulp and Paper Industry. The cleaning solvent supply orifice 308 allows the electrodes 302 to be cleaned periodically without needing to remove the electrodes 302. The method of cleaning the electrodes 302 may involve several different cleaning or rinsing cycles and/or purge cycles to remove the cleaning solvent from the electrodes 302. pulp liquor used in the Pulp and Paper Industry. The cleaning solvent supply orifice 308 allows the electrodes Referring to FIG. 4, an exploded view of an exemplary embodiment of a probe assembly 400 used for analyzing pulp liquor at a paper mill is shown. The probe body weldment 402 is the portion of the probe assembly 400 that is sealably mounted to the digester or recausticizing tank 102. An electrode housing 404 (such as the electrode housing 300 shown in FIG. 3) is sealably coupled to the end of the probe assembly that is inserted into the digester or recausticizing tank 102.

Figure 5:
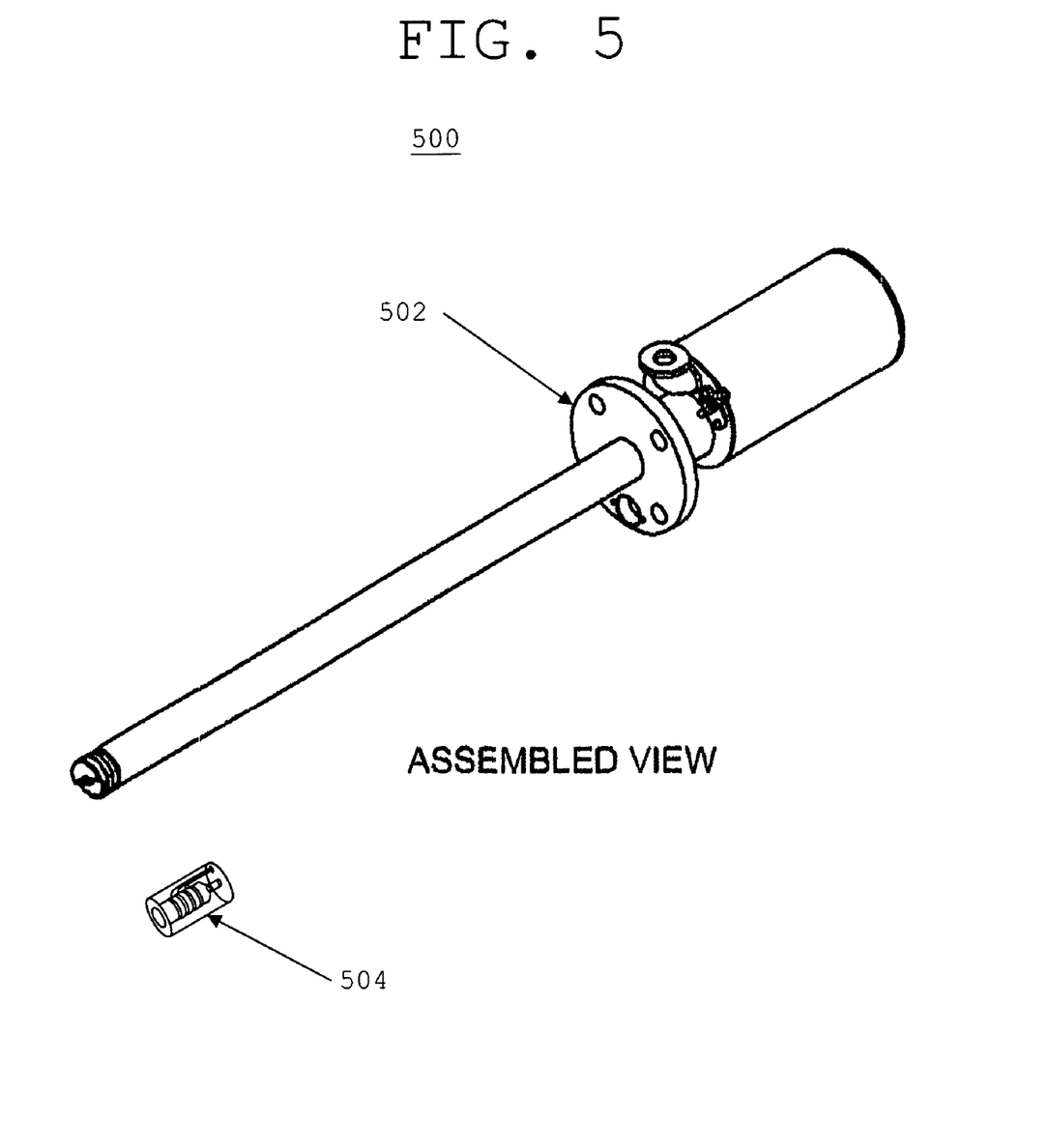
FIG. 5 is an assembled view of a sensor housing design, including a cleaning system, according to an exemplary embodiment of the invention.

Referring to FIG. 5, an assembled view of an exemplary embodiment of a probe assembly 500 used for analyzing pulp liquor at a paper mill is shown. The probe body weldment 502 is the portion of the probe assembly 500 that is sealably mounted to the digester or recausticizing tank 102. An electrode housing 504 (such as the electrode housing 300 shown in FIG. 3) is sealably coupled to the end of the probe assembly that is inserted into the digester or recausticizing tank 102.

Figure 6:
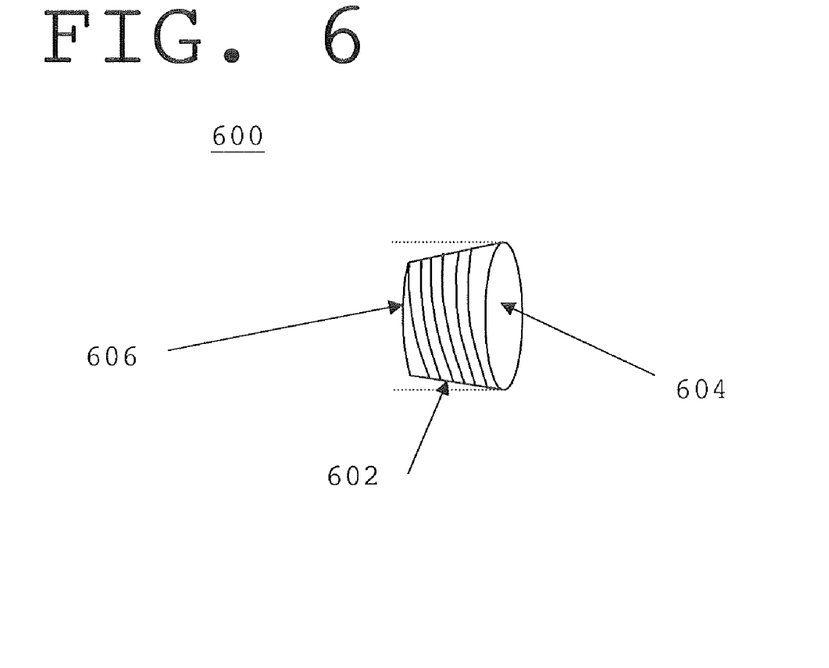
FIG. 6 is a generalized schematic of the electrode according to a third exemplary embodiment of the invention.

Referring to FIG. 6, an exemplary electrode 600 for sensing characteristics of a liquid according to a third exemplary embodiment is shown. The electrode 600 contains a tapered thread portion 602 on the coupling portion of the electrode 600. Also contained on the coupling portion of the electrode 600 may be an electrical coupling 606 used for communicating an electrical signal from the electrode 600. The electrical signal is routed from the electrode 600 through an electrode housing and out to the desired receiving equipment external to the liquid. The electrode 600 also has a sensor portion 604 that is in direct contact with the liquid to be measured. In this exemplary embodiment, the electrode sensing surface 604 is a smooth surface and, once assembled to an electrode housing, this surface 604 may be flush with the surface of the housing.

The tapered thread portion 602 may provide a tight seal to isolate the electrode sensing surface 604 from the electrical coupling 606. An assembly specification may provide a torque measurement to ensure that once assembled, there will be a suitable seal between the electrode sensing surface 604 and the electrical coupling 606. In another exemplary embodiment, the tapered thread portion 602 of the electrode 600 may be coated with urethane to further seal the electrical coupling 606 from the electrode sensing surface 604.

Referring to FIG. 6, an exemplary embodiment of the electrode 600 has an electrode sensing surface 604 that is circular in shape, and the electrode 600 mounts flush with an electrode housing. These features may be altered without affecting the applicability of the present invention. The electrode 600 may be composed of platinum or another inert conductive material, such as gold, graphite, iridium, palladium, or carbon. Other materials such as stainless steel and titanium are possible in certain situations.

Figure 7:
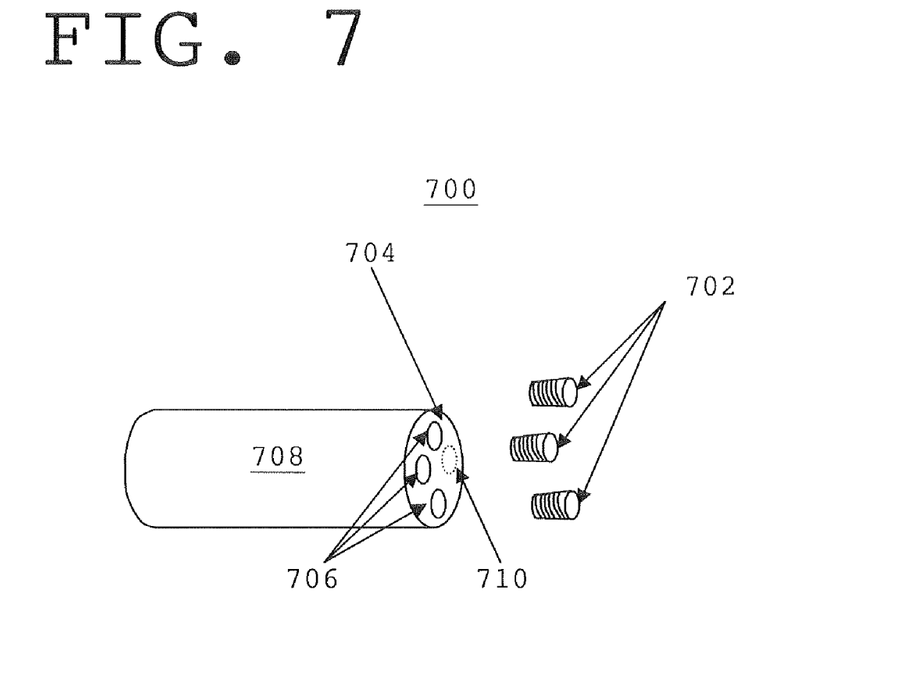
FIG. 7 is a generalized schematic of an electrode housing design according to a fourth exemplary embodiment of the invention.

Referring to FIG. 7, a fourth exemplary embodiment of an electrode housing assembly 700 is shown. Electrodes 702 may be similar to the individual electrode 600 previously described. The electrodes 702 may be assembled to an electrode housing 708 to provide the electrode housing assembly 700. In this exemplary assembly, there are three electrodes 702 arranged on one half of the circular electrode housing surface 704; however, the electrode housing assembly 700 is not limited to any specific quantity or arrangement of electrodes 702. The arrangement shown allows for a cleaning system to be incorporated into the electrode housing assembly 700 which would extend the usable life of the electrodes 702. One possible example of such a cleaning system is described in U.S. Pat. No. 6,235,123 issued May 22, 2002, entitled "Chemical Cleaning System For Electrodes Used In A Liquid Environment," which is incorporated herein by reference.

The electrode housing assembly 700 may contain a threaded aperture 706 for receiving the tapered thread of the coupling portion of each electrode 702. Each threaded aperture 706 may also contain an electrical coupling for communicating the electrical signal from each electrode 702. The threaded apertures 706 are contained on a surface 704 of the electrode housing 708. The liquid to be analyzed flows over the electrode housing surface 704 and comes into contact with each electrode's sensing surface (such as with each electrode's sensing surface 604 shown in FIG. 6). The electrical signal generated and/or received by the liquid is transmitted from the electrode sensing surface through the electrode 702 and to the electrical coupling located in the threaded aperture 706 of the electrode housing 708.

The electrode housing assembly 700 allows the electrical signal to be transmitted from a harsh environment to the electrical coupling in the threaded aperture of the electrode housing 708. From the electrode housing 708, the electrical signal is then transmitted to receiving equipment external to the container of liquid that is being analyzed. One possible example of receiving equipment is described in U.S. Pat. No. 6,416,651 issued Jul. 9, 2002, entitled "Multi-Electrode Composition Measuring Device And Method," which is incorporated herein by reference.

The tapered thread portion (such as the tapered thread portion 602 as shown in FIG. 6) of each electrode 702 may contain or be coated with urethane to help minimize the damaging effects of the caustic pulp liquor used in paper processing. The design and material of the tapered thread portion of each electrode 702 may be selected based on the desired operation environment and/or insulating need of the electrodes 702.

According to one exemplary embodiment, the electrode housing 700 contains a cleaning solvent supply orifice 710. The cleaning solvent supply orifice 710 directs a cleaning solvent across the sensing surface of each electrode 702 to remove any accumulations on this surface. The cleaning solvent applied in this manner minimizes the damaging effects on the electrodes 702 due to caustic pulp liquor used in the pulp and paper industry. The cleaning solvent supply orifice 710 allows the electrodes 702 to be cleaned periodically without needing to remove the electrodes 702. The method of cleaning the electrodes 702 may involve several different cleaning or rinsing cycles and/or purge cycles to remove the cleaning solvent from the electrodes 702.

Figure 8:
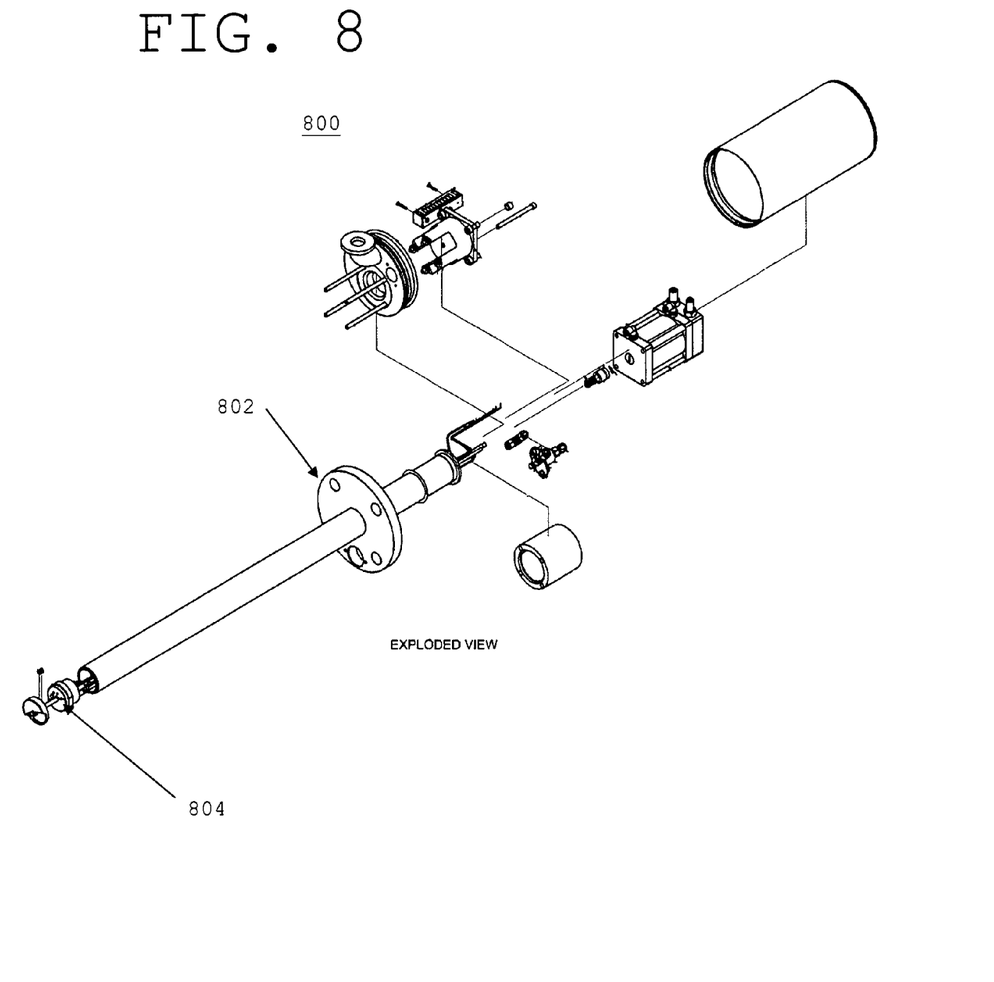
FIG. 8 is an exploded view of a sensor housing design, including a cleaning system, according to an another exemplary embodiment of the invention.

Referring to FIG. 8, an exploded view of another exemplary embodiment of a probe assembly 800 used for analyzing pulp liquor at a paper mill is shown. The probe body weldment 802 is the portion of the probe assembly 800 that is sealably mounted to the digester or recausticizing tank 102. The electrode housing 804 is sealably coupled to the end of the probe assembly that is inserted into the digester or recausticizing tank 102.

Figure 9:
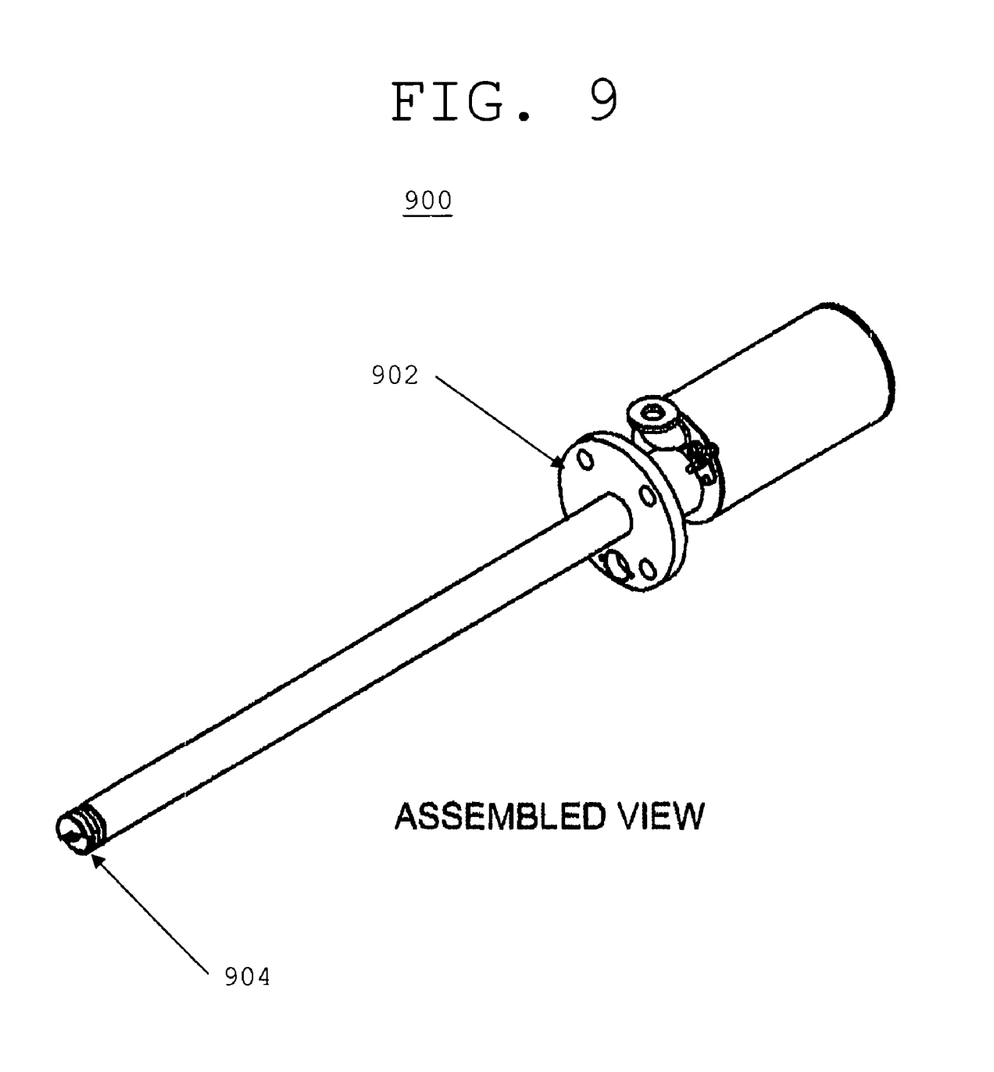
FIG. 9 is an assembled view of a sensor housing design, including a cleaning system, according to an another exemplary embodiment of the invention.

Referring to FIG. 9, an assembled view of another exemplary embodiment of a probe assembly 900 used for analyzing pulp liquor at a paper mill is shown. The probe body weldment 902 is the portion of the probe assembly 900 that is sealably mounted to the digester or recausticizing tank 102. The electrode housing 904 is sealably coupled to the end of the probe assembly that is inserted into the digester or recausticizing tank 102.

It will be understood that the foregoing is only illustrative of the principles of the invention. The exemplary embodiments described herein have been illustrated for use in measuring liquor in the pulp making process; however, the embodiments are not limited to the pulp making process and may be used in a variety of industries. The embodiments are also not limited to measurement of liquid material. The electrodes may be used to measure, for example, semi-liquids or gases. Accordingly, such embodiments will be recognized as within the scope of the present invention.

Persons skilled in the art will also appreciate that the present invention can be practiced by other than the described embodiments, which are presented for purposes of illustration rather than of limitation and that the present invention is limited only by the claims that follow.

What is claimed is:

1. An apparatus for sensing one or more characteristics of a liquid, comprising:
    an electrode configured to receive electrical signals from the liquid, wherein the electrode has (i) a sensor portion configured to contact the liquid and (ii) a coupling portion with a tapered thread; and
    an electrode housing having (i) a threaded aperture configured to receive the tapered thread of the coupling portion of the electrode and (ii) an electrical coupling configured to communicate the electrical signals from the electrode.

2. The apparatus of claim 1, wherein the apparatus comprises two or more of the electrodes, and the electrode housing has two or more threaded apertures configured to receive the tapered threads of the coupling portions of the electrodes.

3. The apparatus of claim 1, wherein the liquid comprises a liquor used in a paper mill process.

4. The apparatus of claim 1, wherein the electrode comprises one of platinum, gold, graphite, iridium, palladium, carbon, stainless steel, and titanium.

5. The apparatus of claim 1, wherein the electrode housing comprises nickel-molybdenum-chromium-tungsten alloy.

6. The apparatus of claim 1, wherein the tapered thread of the electrode is coated with urethane.

7. The apparatus of claim 1, wherein the liquid is corrosive.

8. A system comprising:
a probe body weldment configured to be sealably mounted on a container; and
a sensor assembly mounted on the probe body weldment, the sensor assembly comprising:
an electrode configured to receive electrical signals from a material in the container, the electrode having (i) a sensor portion configured to contact the material and (ii) a coupling portion with a tapered thread; and
an electrode housing having (i) a threaded aperture configured to receive the tapered thread of the coupling portion of the electrode and (ii) an electrical coupling configured to communicate the electrical signals from the electrode.

9. The system of claim 8, wherein:
the sensor assembly comprises two or more of the electrodes; and
the electrode housing comprises two or more threaded apertures configured to receive the tapered threads of the coupling portions of the electrodes.

10. The system of claim 8, wherein the electrode comprises one of platinum, gold, graphite, iridium, palladium, carbon, stainless steel, and titanium.

11. The system of claim 8, wherein the electrode housing comprises a nickel-molybdenum-chromium-tungsten alloy.

12. The system of claim 8, wherein the tapered thread of the electrode is coated with urethane.

13. The system of claim 8, wherein the container comprises at least one of: a tank, a pipe, and a shipping container.

14. The system of claim 8, further comprising:
receiving equipment configured to receive sensor readings from the sensor assembly over at least one wire running through the probe body weldment.

15. The system of claim 8, wherein the sensor portion of the electrode comprises a smooth surface that is flush with a surface of the electrode housing when the electrode is inserted into the threaded aperture of the electrode housing.

16. A method comprising:
inserting an electrode into an electrode housing, the electrode comprising (i) a sensor portion configured to contact a material in a container and (ii) a coupling portion with a tapered thread, the electrode housing comprising a threaded aperture that receives the tapered thread of the coupling portion of the electrode; and
mounting the electrode housing in the container.

17. The method of claim 16, further comprising:
receiving electrical signals from the material in the container at the electrode; and
providing the electrical signals to receiving equipment external to the container.

18. The method of claim 17, wherein providing the electrical signals comprises:
providing the electrical signals from the electrode to the electrode housing; and
providing the electrical signals from the electrode housing to the receiving equipment.

19. The method of claim 16, wherein inserting the electrode into the electrode housing comprises inserting the electrode into the electrode housing such that a smooth surface of the sensor portion of the electrode is flush with a surface of the electrode housing.

20. The method of claim 16, wherein inserting the electrode into the electrode housing comprises sealing the electrode to the electrode housing using a coating of urethane on the tapered thread of the electrode.

* * * * *